United States Patent [19]

Latimer et al.

[11] Patent Number: 5,237,874
[45] Date of Patent: Aug. 24, 1993

[54] ROTATING ELECTROMAGNETIC ACOUSTIC TRANSDUCER FOR METAL INSPECTION

[75] Inventors: Paul J. Latimer, Lynchburg; Gary W. Owens, Rustburg; Nelson Perez, Lynchburg; Christos N. Sarantos, Forest, all of Va.

[73] Assignee: The Babcock & Wilcox Company, New Orleans, La.

[21] Appl. No.: 772,316

[22] Filed: Oct. 7, 1991

[51] Int. Cl.$^5$ .................. G01N 29/10; G01N 29/24
[52] U.S. Cl. .................................... 73/621; 73/633; 73/643; 73/634
[58] Field of Search ................ 73/643, 633, 634, 620, 73/640, 621, 629

[56] References Cited

U.S. PATENT DOCUMENTS

| | | | |
|---|---|---|---|
| 3,996,792 | 12/1976 | Kubota et al. | 73/621 |
| 4,043,185 | 8/1977 | Siebert | 73/621 |
| 4,322,975 | 4/1982 | Schmidt et al. | 73/633 |
| 4,665,752 | 5/1987 | Hüschelrath et al. | 73/643 |
| 4,787,247 | 11/1988 | Wuchinich et al. | 73/633 |
| 5,051,696 | 9/1991 | Schmale | 73/633 |

Primary Examiner—Tom Noland
Assistant Examiner—Rose M. Finley
Attorney, Agent, or Firm—Robert J. Edwards; Michael L. Hoelter

[57] ABSTRACT

This invention pertains to a method and apparatus of non-destructive testing wherein a generally bidirectional wave generating electromagnetic acoustic transducer is pivotally mounted upon a base with this transducer being continuously rotated or oscillated upon the base as it is moved with respect to the workpiece (or the workpiece is moved with respect to the base). This oscillation or rotation causes a wave to be generated along an arc with these waves extending radially outward from the base so that any flaws in the workpiece can be struck at an angle as close to 90 degrees as possible (the optimal incident angle).

20 Claims, 1 Drawing Sheet

ROTATING ELECTROMAGNETIC ACOUSTIC TRANSDUCER FOR METAL INSPECTION

FIELD OF THE INVENTION

This invention pertains to non-destructive testing and more particularly to the use of an oscillating or rotating electromagnetic acoustic transducer (EMAT) for the testing of metal components.

BACKGROUND OF THE INVENTION

In non-destructive testing involving electromagnetic acoustic transducers (EMAT), it is preferable for the flaw to be struck at normal incidence (90 degrees) so that it can be better evaluated and characterized. Unfortunately, however, the wave generation of the transducers typically used are primarily bidirectional, but with some unidirectional characteristics, which hinders the achievement of this ideal because not all flaws are going to be perfectly aligned with the transducer. Thus these transducers are limited when used to inspect large areas.

In the past, non-destructive testing of large components with an EMAT required either multiple sensors at multiple orientations or it required repetitive scans. Multiple sensors were required so that a larger area could be covered per scan while the different orientations were necessary so that returning waves could decipher any flaw that may not be optimally orientated. The method of repetitive scanning necessitated many changes in the orientation of the sensors so that the flaw would be struck as optimally as possible.

As can be seen, each of the above methods try to direct their waves so as to strike and locate flaws as optimally as possible for better identification. While these methods are suitable for small surfaces, they become a burden when the object being tested is large or the time to inspect the workpiece is limited. Thus, utilizing such non-destructive testing methods on large surfaces is both cumbersome and time consuming due to the unidirectional or bidirectional wave generation of the transducers.

It is thus an object of this invention to provide an electromagnetic acoustic transducer whose wave generation is more than uni- or bidirectional. Another object of this invention is to provide a means of non-destructive testing that can cover large areas in a relatively small amount of time. Still another object of this invention is to provide a testing apparatus that will optimally strike the flaw for better identification. A further advantage of this invention is the fact that EMATs do not require an ultrasonic couplant and therefore the combination of an oscillating sensor with no couplant makes it ideal for rapid coverage in applications requiring automated inspections. These and other objects and advantages will become obvious upon further investigation.

SUMMARY OF THE INVENTION

What is disclosed herein is an oscillating or rotating transducer to be used for the non-destructive testing of a workpiece. In one alternative, the EMAT is pivotally secured to a base that is supported by the workpiece. In another alternative, the base is not supported by the workpiece but instead is supported above the workpiece a known distance with this distance being monitored or controlled by a servo system. In any event, the transducer is rotated upon the base, or directly driven by a motor, about an axis that is generally perpendicular to the workpiece thereby causing the transducer to generate waves that project radially outward from this axis. While this is occurring, either the transducer is moved with respect to the workpiece, the workpiece is moved with respect to the transducer, or both are moved so that the workpiece may be inspected and/or tested for any flaws therein.

DETAILED DESCRIPTION OF THE DRAWING

Figure 1:
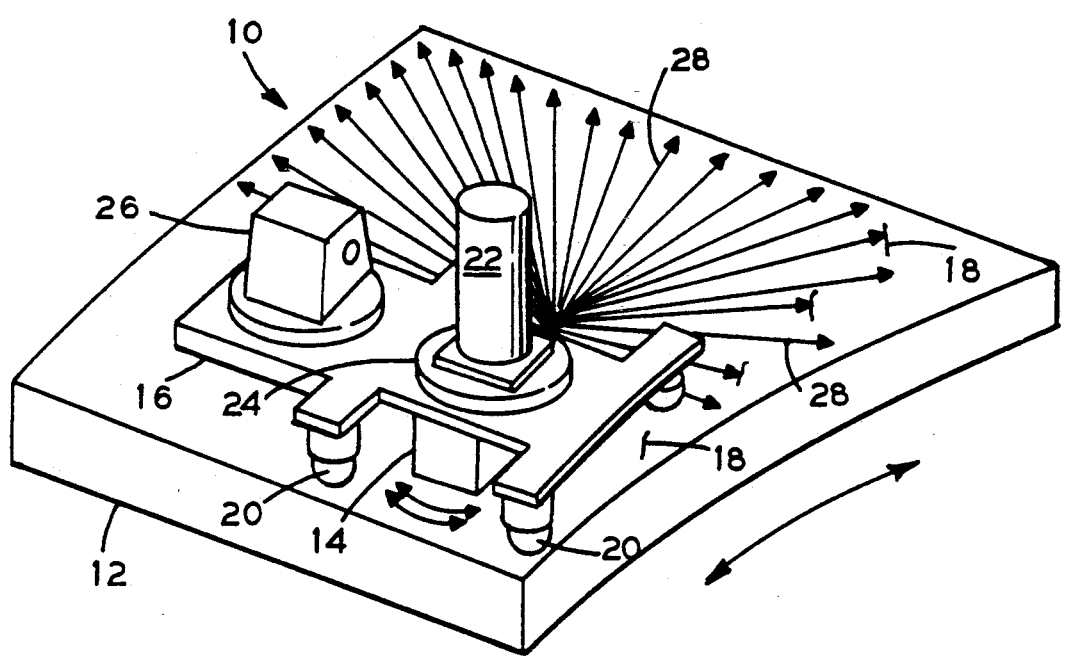
FIG. 1 is a pictorial view of the invention illustrating the range of its wave generation.

Referring to the drawing, there is shown acoustic transducer assembly 10 positioned upon workpiece 12. In this embodiment, workpiece 12 is moved while transducer assembly 10 remains relatively fixed, however, in other embodiments, the reverse can be true or both assembly 10 and workpiece 12 can be moved, whichever is desired. It is also possible for transducer assembly 10 to be spaced a slight distance above workpiece 12 thereby not engaging workpiece 12.

As shown in FIG. 1, transducer 14 oscillates or rotates about an axis that is generally perpendicular to workpiece 12. Because of such rotation or oscillation, transducer 14 generates signals that cover a wide arc. In this embodiment, transducer 14 oscillates about an arc of approximately 180 degrees however lesser or greater arcs are equally possible so is the possibility that transducer 14 will completely rotate about the axis. Thus, assembly 10 generates waves in such a manner that they optimally characterize defects at rapid speeds permitting greater surface coverage.

Transducer 14 is generally a conventional electromagnetic acoustic transducer (EMAT) that has meander coils for the generation of surface and shear waves. While these meander coils are capable of unidirectional wave generation, the waves generated by transducer 14 are almost always bidirectional in actual practice.

As shown, transducer 14 is pivotally mounted upon base 16 (in this embodiment, suspended from the underneath side of base 16) which, as shown, rolls along workpiece 12. Base 16 is configured to remain rigid during use and should workpiece 12 require it, base 16 may even be slightly rounded or arced so as to better conform to the curvature of workpiece 12. This will generally be true even should base 16 not actually engage workpiece 12 or should base 16 be suspended slightly above workpiece 12.

A main purpose of base 16, besides supporting the various hardware, is to position or suspend transducer 14 in such a manner that its generated waves will either project along the surface of workpiece 12 (surface waves) or actually travel within workpiece 12 (shear waves). In this fashion, and due to the rapid rotation or oscillation of transducer 14, any flaws 18 in workpiece 12 will be struck at an angle of nearly 90 degrees, which is the optimal angle of incidence.

It is also conceivable for two transducers 14 to be mounted upon base 16 and oscillated the same, or in unison, thereby making it possible to simultaneously use both shear waves and surface waves to locate flaws 18.

As shown in the embodiment illustrated in FIG. 1, base 16 rolls along workpiece 12 via a series of rollers or ball transfers 20. Rollers 20 are designed to rotate in any direction (360 degree rotation) thereby allowing base 16 and transducer 14 to be moved into any position or location desired with respect to workpiece 12. Rollers 20 also uniformly position base 16 above workpiece 12 a known distance so that transducer 14 may either be mounted or suspended a set distance above workpiece 12 or transducer 14 may actually engage or rest upon workpiece 12 (since sensors generally contact the workpiece) for maximum wave distribution.

Motor or drive 22, which is supported upon base 16, rotates transducer 14 or otherwise causes transducer 14 to oscillate from side to side or rotate continuously. Motor 22, or any other such motion source, is generally mounted on radial and thrust bearings 24 as shown with its rate of rotation being coordinated with the movement of workpiece 12. In this fashion, transducer assembly 10 will be able to locate flaws 18 as well as identify their position within workpiece 12. Adjacent motor 22 on base 16 is quick change tooling adaptor 26 which is used to attach assembly 10 to a manipulator (not shown).

During operation, the oscillation or rotary motion of transducer 14 will generate a series of radial waves 28. These waves 28 will detect flaws 18 in workpiece 12 that are not optimally-oriented to conventional, non-rotating transducers. Thus, the individual defects struck by waves 28 from multiple angles will provide better information about flaw 18 and enable it to be identified and characterized much more accurately. In fact, by gating the instrumentation to transducer 14, a wide band of surface or volume may be investigated. Generally, a scan width of approximately ten inches (more or less) may be possible with transducer assembly 10.

Wire or other leads to transducer assembly 10 are not shown in FIG. 1 for clarity. Suffice it to say, however, that power and control connections to assembly 10 will be needed for operation in addition to devices for deciphering the signals generated by assembly 10. Should a continuously rotating approach be utilized, the power, signal, and control connections would generally be connected to the manipulator (not shown) through slip rings or rotary transformers.

What is claimed is:

1. An apparatus for the non-destructive testing of a workpiece comprising:
(a) a transducer supported by a base with said transducer being pivotable about an axis passing through said transducer, said axis being generally perpendicular to the workpiece;
(b) motor driven rotating means secured upon said base for pivoting said transducer about said axis whereby said transducer generates waves projecting radially outward from said axis; and
(c) moving means for freely and relatively moving either or both said base or the workpiece with respect to each other.

2. The apparatus as set forth in claim 1 wherein said transducer is generally a bidirectional wave generator.

3. The apparatus as set forth in claim 2 wherein said transducer is an electromagnetic acoustic transducer.

4. The apparatus as set forth in claim 3 further comprising radial and thrust bearings for connecting said motor driven rotating means to said transducer.

5. The apparatus as set forth in claim 4 wherein said transducer achieves a scan width of approximately ten inches.

6. The apparatus as set forth in claim 5 wherein said transducer is supported from the underneath side of said base.

7. The apparatus as set forth in claim 6 wherein said base rests upon and said transducer engages and generally conforms to the surface of the workpiece.

8. The apparatus as set forth in claim 7 further comprising roller means for supporting said base upon the workpiece and for maintaining said transducer at the proper elevation with respect to the workpiece.

9. The apparatus as set forth in claim 6 wherein said base does not engage the workpiece but instead is maintained a slight distance above the workpiece.

10. The apparatus as set forth in claim 6 wherein the workpiece remains relatively fixed and said base is moved with respect to the workpiece.

11. The apparatus as set forth in claim 6 wherein said base remains relatively fixed and the workpiece is moved with respect to said base.

12. A method of non-destructive testing of a workpiece comprising the steps of:
(a) mounting a transducer onto a base;
(b) automatically rotating said transducer with respect to said base about an axis passing through said transducer, said axis being generally perpendicular to the workpiece, thereby generating waves which radiate outward away from said base and said axis, said step of automatically rotating said transducer being motor driven; and,
(c) freely and relatively moving said base or the workpiece with respect to each other.

13. The method as set forth in claim 12 wherein said transducer is an electromagnetic acoustic transducer whose wave generation is generally bidirectional.

14. The method as set forth in claim 13 wherein said base supports motor means for rotating said transducer with respect to said base, said motor means comprising radial and thrust bearings.

15. The method as set forth in claim 14 further comprising the step of rotating said transducer to scan a width of about ten inches along the workpiece.

16. The method as set forth in claim 15 further comprising the step of mounting said transducer onto the underneath side of said base.

17. The method as set forth in claim 16 wherein said waves radiate outward along the surface of the workpiece or into the workpiece.

18. The method as set forth in claim 17 wherein said base comprises roller means for supporting said base upon the workpiece and for maintaining said transducer at the proper elevation with respect to the workpiece.

19. The method as set forth in claim 17 wherein the workpiece remains relatively fixed and said base is moved with respect to the workpiece.

20. The method as set forth in claim 17 wherein said base remains relatively fixed and the workpiece is moved with respect to said base.

* * * * *